United States Patent
Westenfelder

(10) Patent No.: US 8,067,365 B2
(45) Date of Patent: Nov. 29, 2011

(54) ERYTHROPOIETIN FOR TREATMENT OF MULTI-ORGAN FAILURE

(75) Inventor: Christof Westenfelder, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 0 days.

(21) Appl. No.: 11/791,287

(22) PCT Filed: Nov. 22, 2005

(86) PCT No.: PCT/US2005/042580
§ 371 (c)(1),
(2), (4) Date: May 21, 2007

(87) PCT Pub. No.: WO2006/055973
PCT Pub. Date: May 26, 2006

(65) Prior Publication Data
US 2007/0293421 A1     Dec. 20, 2007

Related U.S. Application Data

(60) Provisional application No. 60/630,521, filed on Nov. 22, 2004.

(51) Int. Cl.
*A61K 38/18*     (2006.01)
(52) U.S. Cl. .......................................... 514/7.7; 530/399
(58) Field of Classification Search .................. None
See application file for complete search history.

(56) References Cited

U.S. PATENT DOCUMENTS

| | | | |
|---|---|---|---|
| 6,531,121 B2 | 7/2002 | Brines et al. | |
| 6,784,154 B2 | 5/2003 | Westenfelder | |
| 2002/0065214 A1 | 5/2002 | Iaina et al. | |
| 2003/0104988 A1* | 6/2003 | Brines et al. | 514/8 |
| 2005/0075287 A1 | 4/2005 | Van Gilst | |

OTHER PUBLICATIONS

Wells, J.A. Additivity of Mutational Effects in Proteins. Biochemistry 29:8509-8517 (1990).*
Ngo et al. Computational Complexity, Protein Structure Prediction and the Levinthal Paradox. The Protein Folding Problem and Tertiary Structure Prediction, pp. 433-440 and 492-495 (1994).*
Bahlmann et al. Low-dose therapy with the long-acting erythropoietin analogue darbepoietin alpha persistently activates endothelial Akt and attenuates progressive organ failure. Circulation vol. 110:1006-1012 (published on line Aug. 9, 2004).*
Coleman et al. Science review: Recombinant human erythropoietin in critical illness: a role beyond anemia? Critical Care 8:337-341 (available online Jun. 16, 2004).*
Parke et al. Multiple organ dysfunction syndrome. Inflammopharmacology, vol. 11, No. 1, pp. 87-95 (2003).*
Gabriel et al. High-dose recombinant human erythropoietin stimulates reticulocyte production in patients with multiple organ dysfunction syndrome. Journal of Trauma 44(2):361-7 (Feb. 1998).*

* cited by examiner

*Primary Examiner* — Elizabeth C Kemmerer
*Assistant Examiner* — Regina M Deberry
(74) *Attorney, Agent, or Firm* — Ballard Spahr LLP

(57) ABSTRACT

The compositions and methods disclosed herein are for prevention or treatment of multi-organ failure with erythropoietin. The usefulness of the present invention is that erythropoietin may act to prevent the onset of MOF in a patient at risk of developing it. The present invention may further lessen the effect in one or more affected organs in a patient at risk of developing MOF or in one already diagnosed with it.

13 Claims, No Drawings

ERYTHROPOIETIN FOR TREATMENT OF MULTI-ORGAN FAILURE

CROSS-REFERENCE TO RELATED APPLICATIONS

The present application is a U.S. national phase filing under 35 U.S.C. 371 of International Patent Application No. PCT/US2005/042580, filed Nov. 22, 2005, which claims the benefit of U.S. Provisional Patent Application No. 60/630,521, filed Nov. 22, 2004, each of which are hereby incorporated by reference in their entirety.

STATEMENT OF FEDERAL FUNDING

The subject matter described herein was in-part made possible by support from the Department of Veterans Affairs, Dialysis Research Foundation, National Kidney Foundation of Utah, and The Heart, Lung and Blood Institute of the NIH. The government may have certain rights in the invention.

FIELD OF THE INVENTION

The present compositions and methods relate to the field of medicine. More particularly, the disclosed compositions and methods concern the use of pharmaceutical compositions comprising erythropoietin for treatment or prevention of multi-organ failure.

BACKGROUND OF THE INVENTION

Multi-organ failure (MOF) is the rapid and often sequential degeneration of function of at least two organs in a patient that, most often, results in the death of 4 out of 5 patients who suffer from it. MOF can result from trauma, infection or disease initially associated with one organ (e.g., acute renal failure, respiratory infection, pancreatitis, and the like) or from conditions that present systemically (e.g., sepsis, major burns, sickle cell anemia, premature birth, excessive blood loss, chemotherapy and the like). Contributory factors of MOF include hypoxia, increased intestinal permeability, bacterial translocation, endotoxaemia, infection and uncontrolled systemic inflammatory responses.

Erythropoietin is a glycoprotein hormone critical to the enhanced survival (anti-apoptotic action), proliferation (mitogenesis) and differentiation of bone marrow erythroid progenitor cells. In this way erythropoietin controls the number of red blood cells in the circulation and hence the oxygen-carrying capacity of the blood. The peripheral red cell count is kept constant by a controlled feedback mechanism involving oxygen supply, erythropoietin secretion and erythropoiesis. However, the system can become unbalanced in an individual suffering from MOF.

Due to the high fatality rate associated with MOF, a novel strategy is greatly needed to prevent the onset of MOF in a patient at risk of developing it, as well as a method of treating those patients who have already have it.

SUMMARY OF THE INVENTION

The methods of the present invention provide a method of preventing MOF in a patient at risk of developing it by the administration of a therapeutically effective amount of a pharmaceutical composition including erythropoietin (EPO) and a pharmaceutically acceptable carrier.

The methods of the present invention also provide a method of treating MOF in a patient by the administration of a therapeutically effective amount of a pharmaceutical composition comprising EPO and a pharmaceutically acceptable carrier.

The EPO of the present invention may be selected from the group consisting of recombinant human EPO, an EPO analog, a modified EPO, an EPO derivative, an EPO mimetic, and the like.

The pharmaceutical compositions of the present invention may be administered systemically.

In one embodiment, the pharmaceutical compositions of the present invention may be administered in subpolycythemic doses. In a particular embodiment, the subpolycythemic dose is administered from two to five times over a period of two to five days. In another particular embodiment, the doses may be administered 24 hours apart. In a third particular embodiment, the subpolycythemic doses may include between 250-5000 U/kg body weight EPO in said pharmaceutical composition.

The patient at risk for developing multi-organ failure may have a condition selected from the group consisting of diabetes, renal insufficiency, acute renal failure, respiratory infection, pancreatitis, old age, pending surgery, recent injury, major burns, sickle cell anemia, premature birth, excessive blood loss, chemotherapy, atherosclerotic disease, administration of a nephrotoxic agent, sepsis, hypotension, hypoxia and liver disease. In a particular embodiment, the condition is acute renal failure.

The pharmaceutical compositions of the present invention may be administered to the patient at risk of developing MOF prior to a condition including surgery, administration of a nephrotoxic agent, chemotherapy and the like.

In an embodiment, the administration of the pharmaceutical composition prevents failure in one or more additional organs.

In another embodiment, the administration of a pharmaceutical composition of the present invention lessens the damage to one or more additional organs.

Another embodiment provides, the administration of a pharmaceutical composition of the present invention to improve a function selected from the group consisting of renal, lung, liver and the like. In a particular embodiment, the improvement in lung function is selected from the group consisting of lowered levels of edema, improved histological injury score, lowered levels of inflammation, and the like. In another particular embodiment, the improvement in liver function is selected from the group consisting of lowered liver enzymes and repair of cell injury.

DETAILED DESCRIPTION OF THE INVENTION

The present invention provides compositions and methods for treating or preventing MOF by administration of a pharmaceutical composition including EPO. The dosage and duration of treatment will depend on such factors as the progression of the disease, condition that presents a risk of developing MOF, the age and general health of the patient, the response of the individual to the initial administration, the potency of the EPO administered the severity of side effects and the like. In a particular embodiment, administration will last for at least 5 days. In another particular embodiment, the invention provides for the administration of a pharmaceutical composition including between 250-5000 U/kg (unit per kilogram) body weight of recombinant human EPO, or a corresponding amount of an analog, mimetic or derivative with an activity equivalent to about 250-5000 U/kg recombinant human EPO, to a patient diagnosed with MOF or in danger of developing MOF. One of skill in the art can readily determine the appropriate EPO dosage and duration of treatment for a particular patient.

DEFINITIONS

For the purposes of the present invention, the following terms shall have the following meanings:

For the purposes of the present invention, the terms "multi-organ failure", "multiple organ failure", "multi-system organ failure," "MOF" and "multi-organ dysfunction" shall refer to a rapid and often sequential degeneration of function affecting at least two major organs of the body.

For the purposes of the present invention, the term "erythropoietin" or "EPO" shall refer to synthetic or recombinant erythropoietin, erythropoietin isolated from natural sources, erythropoietin analogs, EPO receptor agonists, erythropoietin mimetics, an erythropoietin fragment, a hybrid erythropoietin molecule, an erythropoietin receptor-binding molecule, an erythropoietin agonist, human or another mammalian erythropoietin, an oligomer of any of the foregoing, a mutein of any of the foregoing, a congener of any of the foregoing, a glycosylation variant of any of the foregoing, a deglycosylated variant of any of the foregoing, or a combination of any of the foregoing.

For the purposes of the present invention, the terms "individual", "patient", and "subject" are to mean a mammal of either gender. In a particular embodiment, the mammal is a human.

For the purposes of the present invention, the terms "ischemia" or "ischemic" refer to poor blood supply to an organ for any reason. Exemplary reasons for poor blood supply include multiple bodily injuries, infections, septicemia, internal or external hemorrhaging, severe loss of fluid, transfusion reactions, heart attack, organ transplantation, surgical shock and the like.

For the purposes of the present invention, the term, "therapeutically effective amount" and "therapeutically effective dose" refers to a dose of a composition of the present invention sufficient to treat or prevent MOF in a patient. The dose will be easily determined by a physician skilled in the art of treating patients with MOF or those at risk of developing it and may vary from patient to patient.

For the purposes of the present invention, ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

Moreover, for the purposes of the present invention, the term "a", "an" or "the" refers to one or more of that entity; for example, "a composition" or "an organ" refers to one or more of those elements or at least one of those elements. As such, the terms "a" or "an", "one or more" and "at least one" can be used interchangeably herein. It is also to be noted that the terms "comprising", "including", and "having" can be used interchangeably.

Furthermore, a compound "selected from the group consisting of" refers to one or more of the compounds in the list that follows, including mixtures (i.e. combinations) of two or more of the compounds. According to the present invention, an isolated or biologically pure EPO molecule is a compound that has been removed from its natural milieu. As such, "isolated" and "biologically pure" do not necessarily reflect the extent to which the compound has been purified. An isolated compound of the present invention can be obtained from its natural source, can be produced using molecular biology techniques or can be produced by chemical synthesis or modification.

There are many exemplary clinical indicators of MOF and a physician skilled in the art is capable of making such a diagnosis. Such exemplary clinical indicators include a body temperature that may range from a fever, closely followed by hypothermia; bradycardio; hypotension; ventricular tachycardia; ventricular fibrillation; metabolic acidosis; hypercapnia; hypoxaemia; and a respiratory rate of less than 5 or more than 50 breaths per minute. Other indicators may include urine output of less than 400 ml per 24 hours and a serum creatinine level less than 150 mmol/L. A patient may also demonstrate leucopenia, thrombocytopenia, evidence of disseminated intravascular coagulation and the like. Hepatic factors may include a coagulation defect and high levels of hepatic enzymes and bilirubin. Gastrointestinal factors may include ileus, gastroparesis, hemorrhage and the like. Neurological factors may include a depressed level of consciousness, such as a Glasgow coma score of less than 6, seizures and the like. Additional manifestations characteristic of MOF will be recognized by those skilled in the art.

Current protocols for treating multi-organ failure are mainly a matter of "damage control" and a physician typically addresses individual organs or systems, rather than MOF in itself. For example, pressors and fluids are administered to improve blood pressure and circulation; oxygen may be prescribed for hypoxia, anticoagulants for disseminated intravascular coagulation and antibiotics for significant infections. Additionally, frequent hemodialysis or continuous renal replacement therapy (CRRT), the former resulting in rapid control of body fluid volume and the latter in slow control of body fluid volume, may be instituted for improvement of the uremic state and its complications.

The present invention provides novel methods of treating or preventing MOF itself, rather than merely the effects of the disease on individual organs or systems of the body. The methods of the present invention provide for the administration of a pharmaceutical composition including EPO to treat MOF in a patient diagnosed with it. The methods of the present invention also provide for the administration of a pharmaceutical composition including EPO to prevent MOF in a patient at risk of developing it. Such administration may further prevent the involvement of additional organs or decrease the effect of MOF upon additional organs that become involved.

The disclosed methods provide levels of EPO high enough to treat or prevent MOF but not so high as to cause unwanted side effects, such as hypertension and thromboembolism.

The methods of the present invention also include treatment of patients at risk for developing MOF. Patients at risk for developing MOF, may have a condition selected from the group consisting of, diabetes, renal insufficiency, acute renal failure, respiratory infection, pancreatitis, old age, pending surgery, recent injury, major burns, sickle cell anemia, premature birth, excessive blood loss, chemotherapy, atherosclerotic disease, administration of a nephrotoxic agent, sepsis, hypotension, hypoxia and liver disease, and the like.

In a particular embodiment, such condition is acute renal failure or renal insufficiency. The methods of the present invention may replace or supplement EPO levels in a patient with low levels due to damage to one or more organs. As the kidney produces much of the EPO for the entire body, if there is damage to this organ due to renal insufficiency or chronic renal failure, such supplementation may be needed to prevent the onset of MOF or lessen its effects if a patient already has it. As such, administration of a pharmaceutical composition including EPO of the present invention can normalize the body's EPO levels when renal function is impaired in order to prevent the onset of MFO or lessen its effects on other organs or systems in a patient that already has been diagnosed with it.

A patient at risk of developing MOF or who already has been diagnosed with MOF may be administered a subpolycythemic dose of EPO. This dose is preferred as administration of EPO at greater than subpolycythemic doses may cause polycythemia and other negative reactions, such as renal vasoconstriction, hypertension, thromboembolism, and the like. In a particular embodiment, the invention provides for the administration of a pharmaceutical composition including a unit dose between about 250-5000 U/kg body weight of EPO, or a corresponding amount of an analog, agonist, mimetic or derivative with an activity equivalent to about a unit dose of 250-5000 U/kg EPO.

In patients at risk for developing MOF, administration of a therapeutically effective amount of a pharmaceutical composition including EPO may prevent the onset of MOF. In one embodiment, administration includes a subpolycythemic dose of EPO prior to an event that may cause MOF. In a particular embodiment, a patient at risk of developing MOF is administered a pharmaceutical composition including EPO up to six hours before the event. Multiple administrations over a given period of time may further prevent the onset of MOF in a patient at risk of developing it. In a particular embodiment, such administration includes a unit dose of between 250-5000 U/kg body weight of EPO up to six hours prior to an event or upon the realization that such patient may be at risk for developing MOF. Such administration may be thereafter repeated to further provide protection from the development of MOF in such a patient. In a particular embodiment, such administration is repeated every 24 hours after the initial dose. Events that may put a patient at risk for developing MOF include surgery, administration of a nephrotoxic agent, chemotherapy and the like. Additionally, MOF may also be prevented in patients displaying one or more of the clinical indicators for the disease by administering a pharmaceutical composition of the present invention.

The administration of a pharmaceutical composition of the present invention to a patient at risk of developing MOF may prevent the involvement of additional organs in a patient at risk of developing MOF. Alternatively, administration of a pharmaceutical composition including EPO of the present invention may lessen the effect on one or more additional organs that do become affected in a patient at risk of developing MOF that is later diagnosed with MOF.

The methods of the present invention also include the treatment of patients already diagnosed with MOF. A patient with MOF may display one or more of the clinical indicators associated with the diagnosis of MOF. The patient may be administered a therapeutically effective amount of a pharmaceutical composition including EPO. The administration may be repeated as often as is medically necessary. In a particular embodiment, the pharmaceutical composition including EPO is administered every 24 hours. In another particular embodiment, a patient is administered a subpolycythemic dose of EPO. In a third particular embodiment, administration includes a unit dose of between 250-5000 U/kg body weight of EPO that may be repeated every 24 hours.

Another embodiment of the present invention provides the administration of a pharmaceutical composition of the present invention to improve a function selected from the group consisting of renal, lung, liver and the like. In a particular embodiment, the improvement in lung function is selected from the group consisting of lowered levels of edema, improved histological injury score, lowered levels of inflammation, and the like. In another particular embodiment, the improvement in liver function is selected from the group consisting of lowered liver enzymes and repair of cell injury.

It will be understood by one of skill in the art that the specific unit dose and treatment protocol for any particular patient may be varied and depends upon a variety of factors, including the activity of the specific EPO compound employed; the metabolic stability and length of action of the compound; the age, body weight, general health, sex, and diet of the patient; the mode and time of administration; the rate of excretion; the drug combination being administered to the patient; the severity of the particular condition and any other factor pertinent to the patient undergoing therapy according to a method of the present invention.

Pharmaceutical Compositions and Routes of Administration

Aqueous compositions of the present invention include an effective amount of therapeutic EPO dissolved or dispersed in a pharmaceutically acceptable carrier or aqueous medium. The phrases "pharmaceutically or pharmacologically acceptable" refer to molecular entities and compositions that do not produce an adverse, allergic or other untoward reaction when administered to an animal, or a human, as appropriate. The compositions of the present invention may include a pharmaceutically acceptable carrier.

Aqueous compositions of the present invention comprise an effective amount of the compound, dissolved or dispersed in a pharmaceutically acceptable carrier or aqueous medium. Such compositions can also be referred to as inocula. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions. For human administration, preparations should meet sterility, pyrogenicity, general safety and purity standards as required by FDA and other regulatory agency standards.

The active compounds will generally be formulated for parenteral administration, e.g., formulated for injection via the intravenous, intramuscular, subcutaneous, or intraperitoneal routes. The preparation of an aqueous composition that contains an active component or ingredient will be known to those of skill in the art in light of the present disclosure. Typically, such compositions can be prepared as injectables, either as liquid solutions or suspensions; solid forms suitable for use in preparing solutions or suspensions upon the addition of a liquid prior to injection can also be prepared; and the preparations can also be emulsified.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. All pharmaceutical forms must be stable under the conditions of manufacture and storage and must be preserved against the contaminating action of microorganisms, such as bacteria, fungi and viruses.

Solutions of the active compounds can be prepared in water suitably mixed with a surfactant, such as hydroxypropylcellulose. Dispersions can also be prepared in glycerol, liquid polyethylene glycols, and mixtures thereof, and in oils. Under ordinary conditions of storage and use, these preparations contain a preservative to prevent the growth of microorganisms.

The carrier can also be a solvent or dispersion medium containing, for example, water, ethanol, polyol (for example, glycerol, propylene glycol, liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. In the case of microparticles, an aqueous suspending medium may optionally contain a viscosity enhancer such as sodium carboxymethylcellulose and optionally a surfactant such as Tween-20. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by incorporation in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the particular methods of preparation are vacuum-drying and freeze-drying techniques which yield a powder of the active ingredient plus any additional desired ingredient from a previously sterile-filtered solution thereof. The preparation of more, or highly, concentrated solutions for direct injection is also contemplated, where the use of DMSO as solvent is envisioned to result in extremely rapid penetration, delivering high concentrations of the active agents to a small area.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media that can be employed will be known to those of skill in the art in light of the present disclosure. The term "unit dose" refers to physically discrete units suitable for use in a subject, each unit containing a predetermined quantity of the therapeutic composition calculated to produce the desired responses, discussed above, in association with its administration, i.e., the appropriate route and treatment regimen. The quantity to be administered, both according to number of treatments and unit dose, depends on the subject to be treated, the potency of the recombinant human EPO or EPO analog, agonist, derivative or mimetic, the state of the subject and the protection desired. The person responsible for administration will, in any event, determine the appropriate dose and dosing schedule for the individual subject.

In addition to the compounds formulated for parenteral administration, such as intravenous or intramuscular injection, other alternative methods of administration of the present invention may also be used, including but not limited to intradermal administration, pulmonary administration, buccal administration, transdermal administration and transmucosal administration. All such methods of administration are well known in the art.

EXAMPLES

The following examples are included to demonstrate particular embodiments of the invention. It should be appreciated by those of skill in the art that the techniques disclosed in the examples which follow represent techniques discovered by the inventor to function well in the practice of the invention, and thus can be considered to constitute particular modes for its practice. However, those of skill in the art should, in light of the present disclosure, appreciate that many changes can be made in the specific embodiments which are disclosed and a like or similar result may still be obtained without departing from the spirit and scope of the invention.

Example 1

Prevention and/or a Lessening of the Effects of MOF in Rats at Risk of Developing MOF Experimental Design The following example demonstrates the treatment effect of EPO in a patient with MOF. Chronic renal insufficiency and failure (CRF) was induced in rats by right nephrectomy (kidney extirpation) and left selective renal artery branch ligation. In this fashion the total remaining renal mass was reduced by ~80%, resulting in CRF. This situation resembles patients who have CRF due to diabetes mellitus, hypertension, glomerulonephritis, and the like. This group of patients, particularly when elderly, is at extremely high risk for the development of often fatal, irreversible ARF and, subsequently, MOF (80% plus mortality despite use of all available therapies) when exposed to ischemic (shock, sepsis, surgery, trauma and the like) or toxic (drugs, contrast media and the like) renal or systemic insults. Therefore, once animals with CRF, induced in this fashion, recovered, stabilized and were documented to have CRF (assessed by elevated serum creatinine and urea levels), the remaining kidney tissue on the left was ischemically injured by timed ligation of the renal artery branches that provide blood supply to that residual kidney tissue. This ischemic second insult results in "ARF on CRF", associated with 70% mortality within 7 days of initial onset of ARF, from MOF demonstrated by rapidly developing uremia, electrolyte and acid-base abnormalities (high serum potassium, metabolic acidosis), and failure of the liver and lungs. Lung dysfunction becomes manifest by increased accumulation of water (determined by weighing the organ) and by the accumulation of inflammatory cells in capillaries, patchy hemorrhages, and congestion. Liver dysfunction is manifested by increased plasma levels of hepatocellular enzymes (ALT, AST) and histological changes of cell swelling, vacuolization, inflammation and occasional necrosis.

Results

Twelve animals each with severity matched ARF were treated either with EPO (300 U/kg body weight, s.c.) or normal saline, starting within 24 hours of the diagnosis of ARF. Daily injections were continued for 5 days, and outcome between EPO- and vehicle-treated groups was assessed.

Mortality was determined 7 days after ARF. In the vehicle-treated group, 8/12 animals had died and only 2/12 of the EPO treated-group (P<0.001)

Renal function was also assessed and the animals in the vehicle-treated group were found to demonstrate a complete absence of recovery to minimal recovery whereas the EPO-treated group demonstrated significant recovery in survivors (P<0.001);

Lung function was also assessed. In vehicle-treated, there was little to minimal recovery. In the EPO-treated group, there was significant recovery in survivors with near normal lung weights (water content due to edema), improved histological injury scores and decreased inflammation.

Liver function was assessed and the vehicle-treated group demonstrated a complete absence or only a minimal decrease in liver enzymes and repair of cell injury, whereas the EPO-treated group demonstrated significant and rapid, near complete normalization of liver functions and histological injury in survivors.

The results of this experiment indicate that the treatment of severe ARF with a pharmaceutical composition including EPO may prevent the on-set of MOF entirely or lessen the recruitment of one or more additional organs, as well as lessen the effects in organs that do become involved.

What is claimed is:

1. A method of treating multi-organ failure in a patient, comprising:
    administering to said patient a therapeutically effective amount of a pharmaceutical composition comprising recombinant erythropoietin and a pharmaceutically acceptable carrier in order to lessen the damage to multiple organs.

2. The method of claim 1, wherein said erythropoietin is recombinant human erythropoietin.

3. The method of claim 1, wherein said pharmaceutical composition is administered systemically.

4. The method of claim 1, wherein said pharmaceutical composition is administered in subpolycythemic doses.

5. The method of claim 4, wherein said subpolycythemic dose is administered from two to five times over a period of two to five days.

6. The method of claim 5, wherein said subpolycythemic doses are administered 24 hours apart.

7. The method of claim 6, wherein said subpolycythemic doses include between 250-5000 U/kg body weight recombinant erythropoietin in said pharmaceutical composition.

8. The method of claim 6, wherein said subpolycythemic doses include between 250-5000 U/kg body weight erythropoietin in said pharmaceutical composition.

9. The method of claim 1, wherein said patient upon administration of said pharmaceutical composition demonstrates an improvement in a function selected from the group consisting of renal function, lung function and liver function.

10. A method comprising:
    the administration of a subpolycythemic dose of a pharmaceutical composition comprising recombinant erythropoietin and a pharmaceutically acceptable carrier to a patient suffering from multi-organ failure in order to lessen the damage to multiple organs and improve a function selected from the group consisting of renal function, lung function and liver function.

11. The method of claim 10, wherein said erythropoietin is recombinant human erythropoietin.

12. The method of claim 10, wherein said subpolycythemic dose is administered from two to five times over a period of two to five days.

13. The method of claim 12, wherein said subpolycythemic doses are administered 24 hours apart.

* * * * *